United States Patent [19]

Agnihotri

[11] 4,203,742
[45] May 20, 1980

[54] PROCESS FOR THE RECOVERY OF ETHANE AND HEAVIER HYDROCARBON COMPONENTS FROM METHANE-RICH GASES

[75] Inventor: Chaitanya B. Agnihotri, Cedar Knolls, N.J.

[73] Assignee: Stone & Webster Engineering Corporation, Boston, Mass.

[21] Appl. No.: 956,324

[22] Filed: Oct. 31, 1978

[51] Int. Cl.² .................................................. F25J 3/02
[52] U.S. Cl. ........................................... 62/24; 62/28; 62/23; 62/38
[58] Field of Search ................. 62/38, 39, 40, 23, 24, 62/27, 28

[56] References Cited

U.S. PATENT DOCUMENTS

| | | | |
|---|---|---|---|
| 2,303,609 | 12/1942 | Carney | 196/73 |
| 2,307,024 | 1/1943 | Carney | 196/11 |
| 2,775,103 | 12/1956 | Koble et al. | 62/123 |
| 3,292,380 | 12/1966 | Bucklin | 62/23 |
| 3,292,381 | 12/1966 | Bludworth | 62/27 |
| 3,319,428 | 5/1967 | Isaacson | 62/28 |
| 3,405,530 | 10/1968 | Denahan et al. | 62/28 |
| 3,520,143 | 7/1970 | Becker | 62/28 |
| 3,568,460 | 3/1971 | Hoffman et al. | 62/34 |
| 3,626,448 | 12/1971 | Crawford | 62/28 |
| 4,061,481 | 12/1977 | Campbell et al. | 62/38 |
| 4,155,729 | 5/1979 | Gray et al. | 62/23 |

*Primary Examiner*—Norman Yudkoff
*Attorney, Agent, or Firm*—Morgan, Finnegan, Pine, Foley & Lee

[57] ABSTRACT

A process is disclosed for the recovery of ethane and heavier hydrocarbons from a methane-rich gas utilizing an expander, a high pressure demethanizer tower with flashed and expanded vapor and liquid streams, as coolants in heat exchange relationship with the processed hydrocarbon vapors.

18 Claims, 1 Drawing Figure

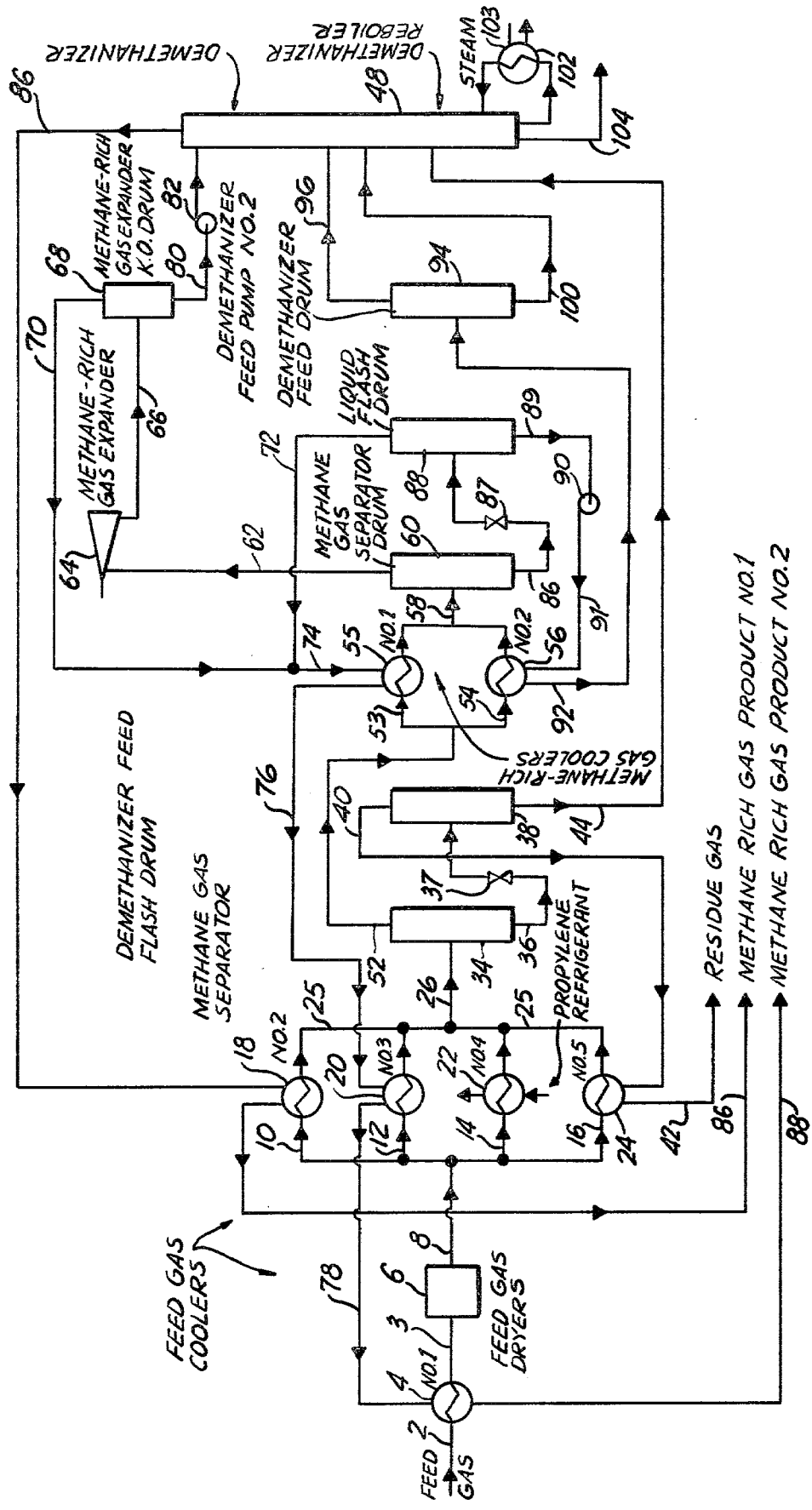

4,203,742

PROCESS FOR THE RECOVERY OF ETHANE AND HEAVIER HYDROCARBON COMPONENTS FROM METHANE-RICH GASES

BACKGROUND OF THE INVENTION

This invention relates generally to a method of processing a gas mixture. More particularly, it relates to a process for recovering ethane and heavier hydrocarbon components from a methane-rich gas.

Methane-rich gases, for example natural gas, usually contain small but significant amounts of higher boiling heavier hydrocarbons such as ethane, propane, butane and the like. These components are quite valuable as feed stock for the manufacture of various petrochemicals and for the production of liquefied petroleum gas. It is therefore desirable to separate these various components prior to sending the lighter gases, i.e., the lean gases that will remain, to the fuel distribution system.

In the conventional process for separating components of natural gas, said components having varying boiling points, the so-called methane cycle is employed. In the conventional low temperature process for the separation of a gas mixture, the gas mixture to be separated is introduced, preferably in the liquid phase, into a rectification tower at about the midpoint thereof, the heavier components being concentrated in the stripping section below the feed point in the column. The vapor mixture within the column at the feed point rises in the upper enrichment section of the column and is enriched in the lower boiling point component. The gases collecting at the top of the column are then in part passed through a high pressure cycle wherein they are compressed, cooled, and liquefied, expanded, and re-introduced into the rectification column as reflux liquid.

SUMMARY OF THE INVENTION

It is therefore an object of the present invention to recover ethane and heavier hydrocarbons from a methane-rich gas, such as a natural gas or gas associated with the oil from off-shore or on-shore drilling operation, whereby the operation of a demethanizing tower is effected with minimum losses of ethane.

Moreover, the process of this invention allows for the maximum possible recovery of ethane and heavier hydrocarbons from a gas which is lean in these constituents.

In addition, the subject process allows substantial savings in energy by utilizing the low level cooling available in the flashed or expanded fluid streams. It also saves energy by pumping the liquid up to the demethanizer tower pressure rather than by expending gas compression horsepower and/or the refrigeration horsepower required for condensing part of the overhead of the low pressure demethanizer tower to provide reflux to this tower.

Accordingly, the present invention is directed to a process for recovering ethane and heavier hydrocarbon components from a methane-rich gas which comprises passing said methane-rich gas through a series of at least two indirect cooling stages and at least two liquid pressure reduction and one turbine expansion stage, resulting in at least three feed streams which are fed to a demethanizer tower wherein ethane and heavier hydrocarbon components are recovered in high yields from gases high in methane content. Vapors and liquids from the liquid pressure reduction stages are used separately as coolants in indirect heat exchange relationship with the hydrocarbon feed gas to effect a partial condensation of the feed. Various liquid and vapor streams obtained by the cooling and pressure reduction stages are fed to the demethanizer tower at the appropriate points. The temperatures of these feed streams is in the range of from about $-50°$ F. to about $-150°$ F. and the pressure in said demethanizer tower is maintained at a level intermediate the pressure of the inlet feed and the pressure at the outlet of said expansion stage.

In the preferred embodiment of the above-described process, feed gas prior to passage to a first separation stage is cooled by one or more coolants in indirect heat exchange relationship therewith.

Preferably, at least one of said coolants is the vapor obtained from a liquid pressure reduction stage.

Preferably, at least one of said coolants is obtained from the demethanizer tower.

Preferably, at least one of said coolants is externally supplied refrigerant which is substantially propylene evaporated at progressively lower temperature levels.

In the preferred embodiment, four feeds are introduced to the demethanizer tower, the first at a temperature of about $-137°$ F., the second and third feeds at a temperature of about $-57°$ F., and the fourth feed at a temperature of about $-50°$ F.

In another aspect of the preferred embodiment, the demethanizer tower is maintained at a pressure in the range from about 350 psia to about 450 psia, and preferably about 410 psia.

In still another aspect of the preferred embodiment, the pressure of the gas at the inlet to said turbine expansion stage is from about 600 psia to about 800 psia and the pressure at the outlet of said expansion stage is from about 300 psia to about 150 psia.

Other objects and a fuller understanding of the invention may be had by referring to the following description and claims taken in conjunction with the accompanying drawing.

BRIEF DESCRIPTION OF THE DRAWING

FIG. 1, a flow diagram, illustrates a process according to the present invention. On this diagram and in the following description routinely employed manual or automatic valves to control process variables such as pressure, temperature and liquid levels are not shown or described. These as well as pumps are shown and described only when they are directly relevant to the invention.

DESCRIPTION OF THE PREFERRED EMBODIMENT

Referring to the figure in detail, a feed gas at about 105° F. and 750 psia is passed by line 2 to the No. 1 feed gas cooler 4 where it is cooled to about 75° F. by a methane-rich gas product No. 2 which enters from heat exchanger 20 through line 78 and is withdrawn through line 88. The gas thus cooled continues through line 3 to feed gas dryer 6 from which it leaves through line 8. Said gas dryer may contain granular activated alumina or silica gel dessicant which is periodically reactivated using equipment and gas streams not shown.

The dried feed gas is additionally cooled to about $-35°$ F. (as described herein below) by passage of portions of it in parallel through the No. 2, 3, 4 and 5 feed gas coolers 18, 20, 22 and 24 by lines 10, 12, 14 and 16 respectively. The portions of gas now associated with liquids which have been condensed in said exchangers are combined in manifold 25 and flow through line 26 to methane gas separator 34 which is maintained at a pressure of about 730 psia.

The hydrocarbon liquid accumulated in separator 34 is passed through line 36 and pressure reduction valve 37 to demethanizer feed flash drum 38. When passing through valve 37 the pressure on the hydrocarbon liquid is reduced to about 475 psia and this results in part of the liquid being evaporated and the temperature dropping to about −50° F. The remaining liquid is separated from the vapor in flash drum 38 and passed through line 44 as the fourth or lowest feed to the demethanizer tower 48. Vapor from flash drum 38 passes through line 40 to the No. 5 feed gas cooler 24 where it cools part of the feed gas as stated hereinabove and is withdrawn as residue gas from the process through line 42.

Vapor from separator 34 flows at about −35° F. through line 52 and then is cooled to about −85° F. by passage of portions of same in parallel through the No. 1 and 2 methane-rich gas coolers 55 and 56 by lines 53 and 54 respectively. The cooled vapor and the liquid condensed by the cooling leave coolers 55 and 56, are combined and through line 58 enter the methane gas separator drum 60 at approximately 700 psia.

The liquid thus entering separator 60 is withdrawn through line 86 and flows through pressure reduction valve 87 into the liquid flash drum 88. When passing through valve 87 the pressure of the liquid is reduced to about 210 psia resulting in some vapor being formed and the temperature being reduced to about −147° F. The vapor is taken off the top of drum 88, is combined with another stream and used in heat exchanger relation with the feed gas as described herein below.

Liquid flows from the bottom of drum 88 through line 89 to pump 90 which raises the pressure of the liquid to about 440 psia. The liquid is discharged from pump 90 through line 91 to the No. 2 methane-rich gas cooler wherein by cooling inlet gas its temperature is raised to about −57° F. and part of the liquid is vaporized. The resulting mixture flows through line 92 to the demethanizer feed drum 94 where vapor and liquid are separated at about 420 psia. The overhead vapor flows from drum 94 through line 96 as the second feed to the appropriate point of the demethanizer tower 48. Liquid from the bottom of drum 94 passes as the third feed through line 100 to its proper point in tower 48.

Vapors from separator 60 pass overhead through line 62 to the methane-rich gas expander 64 wherein energy is abstracted from the vapor as shaft work which with equipment not shown can be employed usefully to compress fluids or generate electric power or can be dissipated as heat. In the expander 64 the vapors are reduced in pressure to about 210 psia and some of the vapor is condensed. The mixture of vapor and liquid at about −130° F. to −150° F. and preferably about −137° F. flows through line 66 to the methane-rich gas expander knockout drum 68. The liquid accumulated in knockout drum 68 is passed through line 80 to pump 82 and enters demethanizer tower 48 as the first feed stream to the demethanizer. Overhead vapor flows from the drum 68 through line 70 and joins with vapors from the liquid flash drum 88 in line 72. The combined vapor stream is used to cool the incoming feed gases. Said gas passes first through line 74 to the No. 1 methane-rich gas cooler 55 where its temperature is raised from about −140° F. to about −47° F. It then passes through line 76, the No. 3 feed gas cooler 20 from which it leaves at about 31° F. through line 78 and enters the No. 1 feed gas cooler 4. The gas, identified as methane-rich gas product No. 2, leaves the No. 1 gas cooler 4 at about 95° F. through line 88 for use external to the invention. Optionally drum 94 can be omitted and the mixture of gas and liquid in line 92 passes directly to tower 48, in which case there will be only three feed streams to the demethanizer tower 48.

It is apparent from the foregoing that there is a multiplicity of feeds to the demethanizer tower 48. The average pressure in tower 48 will preferably be about 409 psia. It will range from about 408 psia at the top to about 410 psia at the bottom. However, it is practicable to operate with the average tower 48 pressure between about 350 psia and 450 psia with the top, bottom and feed point pressures being changed accordingly.

The demethanizer tower 48 may be of conventional bubble cap plate design and contain a number of such plates but other types of plates and vapor-liquid contacting devices may be employed. The bottom part of the tower is shown in FIG. 1 as being heated by a conventional thermosyphon reboiler 102 which is provided with a steam supply 103; however, other types of reboiler and any convenient heat source may be employed.

When operating at the preferred average pressure of about 409 psia the top and bottom temperatures of the demethanizer tower are about −118° F. and 100° F. respectively. Overhead vapors from tower 48 are withdrawn through line 86 and passed to the No. 2 feed gas cooler 18 to cool a portion of the feed gas. They consist mainly of methane with a small amount of ethane and are taken from the processing unit via line 86 as methane-rich gas product No. 1. Bottoms from tower 48 are withdrawn through line 104 and constitute the ethane and heavier product recovered from the natural gas feed. They may be fractionated in equipment not shown into ethane to be used as petrochemical feedstock, $C_3/C_4$ LPG products and a $C_5$ and heavier natural gasoline product.

It should be understood by those skilled in the art that various modifications may be made in the present invention without departing from the spirit and scope thereof as described in the specification and defined in the appended claims.

What is claimed is:

1. A process for recovering ethane and heavier hydrocarbons from a methane-rich gas which comprises:
   (a) passing said gas through a series of at least two indirect cooling stages whereby partial liquefaction of said gas takes place,
   (b) separating the liquid and remaining vapors leaving each indirect cooling stage,
   (c) vaporizing a portion of each of the liquids so formed by passing said liquids through pressure reduction stages,
   (d) separating the vapors from the liquids remaining,
   (e) passing the vapor from the last cooling stage through an expansion turbine whereby part of said vapor is liquefied,
   (f) separating said liquid and remaining vapor,
   (g) passing the liquid remaining after the last liquid pressure reduction stage in heat exchanger relation with a portion of the already partly cooled feed vapor thereby vaporizing a portion of said liquid and forming therefrom a mixture of vapor and liquid, and (h) passing said mixture of vapor and liquid, the liquid from the separator after the expansion turbine and the liquid from the separator following the first liquid pressure reduction stage as separate feed streams to a demethanizer tower, said tower operating at a pressure level intermediate the inlet feed gas pressure and the pressure at the outlet of the expansion turbine.

2. The process of claim 1 wherein the feed gas is dried prior to passage through the first cooling stage.

3. The process of claim 1 wherein the vapor and liquid formed from liquid in step (g) are separated and fed as separate streams to the demethanizer tower.

4. The process of claim 1 wherein the temperatures of the feed streams to the demethanizer tower are in the range of from about $-140°$ F. to about $-50°$ F. and the pressure in said tower is maintained at a level intermediate the pressure of the first liquid pressure reduction stage and the pressure at the outlet of the expansion turbine.

5. The process of claim 4 wherein the vapors from the top of the demethanizer tower are passed in heat exchange relationship with a portion of the gas feed.

6. The process of claim 4 wherein the vapors from the expansion turbine and the vapor from the separation following the last liquid pressure reduction stage are mixed and the mixture is passed in heat exchange relationship in sequence with a portion of the vapors to the last feed vapor cooling stage and a portion of the vapors to another cooling stage.

7. The process of claim 4 wherein the vapors from the separator following the first pressure reduction stage are passed in heat exchange relationship with a portion of the feed gas to the first cooling stage.

8. The process of claim 4 wherein a portion of the feed gas is cooled using refrigeration produced external to the process.

9. The process of claim 8 wherein the feed gas is cooled by refrigerant which is evaporated at progressively lower temperatures.

10. The process of claim 8 wherein the refrigerant is substantially propylene.

11. The process of claim 4 wherein the liquids from the separators following the expansion engine and the second liquid pressure reduction stage are separately withdrawn from their respective separators by means of pumps.

12. The process of claim 4 wherein the first feed fed to the demethanizer tower is introduced at a temperature of about $-137°$ F.

13. The process of claim 4 wherein said second feed mixture fed to the demethanizer tower is introduced at a temperature of about $-57°$ F.

14. The process of claim 4 wherein said third feed fed to the demethanizer tower is introduced at a temperature of about $-50°$ F.

15. The process of claim 4 wherein the demethanizer tower is maintained at a pressure of about 350 to about 450 psia.

16. The process of claim 15 wherein said demethanizer tower pressure is about 410 psia.

17. The process of claim 4 wherein the pressure of the gas at the inlet to the expansion turbine is about 700 psia.

18. The process of claim 4 wherein the pressure of the gas at the outlet of the expansion turbine is about 210 psia.

* * * * *